(12) United States Patent
Gorantla et al.

(10) Patent No.: US 7,943,780 B2
(45) Date of Patent: May 17, 2011

(54) PROCESS FOR THE PREPARATION OF CANDESARTAN CILEXETIL

(75) Inventors: Seeta Ramajaneyulu Gorantla, Secunderabad (IN); Mohan Bandari, Secunderabad (IN); Nageswara Rao Karusala, Secunderabad (IN)

(73) Assignee: Matrix Laboratories Ltd., Secunderabad (IN)

( * ) Notice: Subject to any disclaimer, the term of this patent is extended or adjusted under 35 U.S.C. 154(b) by 177 days.

(21) Appl. No.: 12/279,226

(22) PCT Filed: Feb. 14, 2007

(86) PCT No.: PCT/IN2007/000081
§ 371 (c)(1),
(2), (4) Date: Aug. 13, 2008

(87) PCT Pub. No.: WO2007/094015
PCT Pub. Date: Aug. 23, 2007

(65) Prior Publication Data
US 2009/0018344 A1    Jan. 15, 2009

(30) Foreign Application Priority Data
Feb. 15, 2006   (IN) .............................. 250/CHE/2006

(51) Int. Cl.
*C07D 257/00* (2006.01)
(52) U.S. Cl. ...................................................... 548/253
(58) Field of Classification Search .................. 548/253
See application file for complete search history.

(56) References Cited

U.S. PATENT DOCUMENTS 5,196,444 A * 3/1993 Naka et al. ................. 514/381
2009/0247595 A1* 10/2009 Soldevilla Madrid ........ 514/381

OTHER PUBLICATIONS

EP 0881212A1 (cited in the international search report received on Aug. 13, 2008).*
Szabo et al. (Rapid commun. Mass Spectrom. 2001; 15: 2415-2419).*
March's Advanced Organic Chemistry (5th ed.; 2001, p. 450).*

* cited by examiner

*Primary Examiner* — Yong Chu
*Assistant Examiner* — Valerie Rodriguez-Garcia
(74) *Attorney, Agent, or Firm* — Ladas & Parry LLP

(57) ABSTRACT

The invention relates to process for the preparation of Candesartan cilexetil. More particularly, it relates to the preparation of pure candesartan cilexetil by the deprotection of Trityl candesartan cilexetil with inorganic acids.

9 Claims, No Drawings

PROCESS FOR THE PREPARATION OF CANDESARTAN CILEXETIL

The present invention relates to process for preparation of candesartan cilexetil by detrytilation of Trityl candesartan cilexetil using the inorganic acids.

BACKGROUND OF THE INVENTION

Candesartan cilexetil, 1-[[(Cyclohexyloxy)carbonyl]oxy] ethyl-2-ethoxy-1-[[2'-(1H-tetrazol-5-yl) 1,1'-biphenyl-4-yl]methyl]-1H-benzimidazole-7-carboxylate (Candesartan cilexetil) has the formula as given below

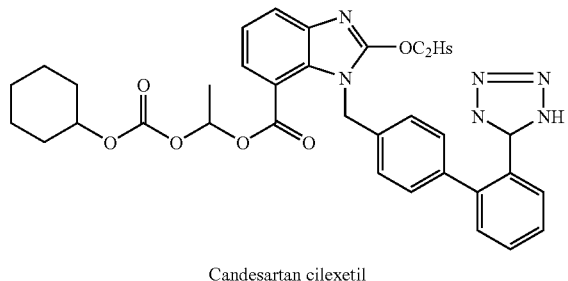

Candesartan cilexetil

Candesartan is a potent, selective AT1 subtype angiotensin II receptor antagonist and used for treatment of hypertension. Due to poor absorption of Candesartan in body, the prodrug candesartan cilexetil was developed. The candesartan cilexetil is rapidly and completely hydrolyzed to candesartan in gastrointestinal tract.

U.S. Pat. No. 5,196,444 discloses Candesartan cilexetil and a process for its preparation by the reaction of 2-ethoxy-[[2'-(1H-tetrazol-5-yl)biphenyl-4-yl]methyl]benzimidazole-7-carboxylic acid with trityl chloride in presence of triethyl amine in methylene chloride and purification by column chromatography gives 2-ethoxy-1-[[2'-(N-triphenylmethyltetrazol-5-yl)-biphenyl-4-yl]methyl]benzimidazole-7-carboxylic acid, which upon condensation with cyclohexyl 1-iodoethyl carbonate in presence of potassium carbonate in DMF followed by purification with column chromatography gives a colorless powder which is recrystallized in ethanol yields 'C' type crystals of Candesartan cilexitil.

U.S. Pat. Application No. 2005/131027 discloses a process for preparation of candesartan cilexetil by reaction of trityl candesartan with cilexetil halide and at least one base in a low boiling solvent in presence of phase transfer catalyst to give Trityl candesartan cilexetil, which upon deprotection with at least one organic acid in at least one organic solvent. U.S. Pat. Application 2005/131027 further discloses the deprotection of Trityl candesartan cilexetil in methanol without an acid.

The PCT publication WO 2005/021535 discloses the deprotection of Trityl candesartan cilexetil with neutral or slightly basic medium in alcohol.

Chem. Pharm. Bull. 47(2), 182-186 (1999) discloses two novel crystalline forms of Candesartan cilexetil, form-I and form-II.

PCT publication WO 04/085426 discloses Candesartan cilexetil 1,4-Dioxane solvate and two more crystalline forms, designated as form-III and form-IV. The disclosed process for preparation of form-III involves crystallization of Candesartan cilexetil in toluene and for form-IV involves crystallization in a mixture of methyl tert-butyl ether and methanol.

PCT publication WO 2005/077941 discloses several crystalline forms, solvates of Candesartan cilexetil along with a process for preparation of form-I (type-C).

The prior art disclosed methods for preparation of Candesartan cilexetil involves purification of Trityl candesartan and Candesartan cilexetil by column chromatography or involves the use of strong acids like 1N HCl or the use of organic acids or without an acid in methanol for detrytilation of Trityl candesartan cilexetil.

There is a requirement of a process for preparation of Candesartan cilexetil which yields a pure Candesartan cilexetil without involving the purification by column chromatography and the usage of strong acids for deprotection.

SUMMARY OF THE INVENTION

The main object of the invention is to develop a process for the preparation of Candesartan cilexetil from Candesartan through Trityl candesartan and Trityl candesartan cilexetil without involving the purification by column chromatography and deprotection of Trityl candesartan cilexetil with inorganic acids.

DETAILED DESCRIPTION OF THE INVENTIONS

Thus in accordance with the present invention preparation of Candesartan cilexetil comprises the following steps;
Treating Candesartan with trityl chloride to get Trityl candesartan
Reacting Trityl candesartan with cilexetil chloride to afford Trityl candesartan cilexetil
Deprotecting Trityl candesartan cilexetil to get Candesartan cilexetil
Recrystallizing Candesartan cilexetil in a mixture of acetone and water to get
type-C crystals In a specific embodiment, the present invention provides a process for the preparation of Candesartan cilexitil, which involves
Dissolving Candesartan in methylene chloride
Adding an organic base preferably triethyl amine
Adding trityl chloride slowly at room temperature
Maintaining the reaction mass at reflux temperature for about 1.5 to 3 hrs
Cooling the reaction mass to 25 to 35° C., and washing the reaction mass with water
Separating the layers and concentrating the separated organic layer.
Adding Ethyl acetate to the residue;
Raising the temperature of the suspension and maintaining at about 45 to 80° C. for about 30 min to 4 hrs.
Cooling the reaction mass to a temperature of about 0 to 20° C. and maintaining for about 30 min to 6 hrs
Isolating the product, washing the wet cake with chilled ethyl acetate and drying to get Trityl candesartan.
Further conversion of Trityl candesartan to Trityl candesartan cilexitil is carried out by
Suspending Trityl candesartan in DMSO
Adding inorganic base selected from potassium carbonate, potassium iodide, sodium carbonate and sodium iodide
Adding Cilexetil chloride slowly over a period of 15 min to 2 hrs at a temperature of about 45° C. to 75° C., preferably at 55° C. to 70° C.
Maintaining the reaction mass at a temperature of about 50° C. to 75° C. for about 1 hr to 3 hrs Adding water and water immiscible hydrocarbon selected from toluene, heptane Separating the layers and extracting the aq. layer with hydrocarbon selected from toluene, heptane Combining the organic layer and removing the solvent under vacuum preferably at temperature of below 75° C.

Adding ethanol to the residue and isolating the trityl candesartan cilexetil.

However, where the intermediate trityl candesartan cilexetil is not isolated the suspension is proceeded directly for the deprotection reaction.

Deprotection of trityl candesartan cilexitil is carried out by

Suspending Trityl cilexetil candesartan in ethanol

Adding inorganic acid(s) selected from phosphoric acid, boric acid

Maintaining the reaction mass at a temperature of 45° C. to reflux temperature for a period for about 6 hrs to 16 hrs Concentrating the reaction mass to about ½ to ¼ volume of original volume, Adding an antisolvent selected from the group $C_5$-$C_7$ hydrocarbon preferably hexane and Heptane at temperature of 20° C. to 65° C.

Maintaining the mass for about 1 hr to 12 hrs at temperature of 10° C. to 55° C. preferably at about 15° C. to 30° C. to get Candesartan cilexitil.

The above obtained Candesartan cilexetil can be converted to stable Type-C crystals by the prior art methods or by the method given below.

Dissolving candesartan cilexetil in acetone at a temperature of 45° C. to 60° C., Removing the insolubles, Adding water preferably in lots, first lot at a temperature of about 35° C. to 45° C. and $2^{nd}$ lot at a temperature of 20° C. to 35° C. and maintaining for about 2 hrs to 6 hrs at room temperature Isolating the product and wash the wet cake with aq acetone Drying the product under vacuum at temperature preferably at about 45° C. to 65° C. to get the Type-C crystals of Candesartan cilexetil.

The obtained type-C crystals are identified by its IR, XRD data.

Methods known in the art may be used with the process of this invention to enhance any aspect of this process. For example the product obtained may be further purified by crystallization from solvent(s). The present invention is further illustrated by the following examples, which are provided nearly to the exemplary of the inventions and is not intended to limit the scope of invention. Certain modifications and equivalents will be apparent to those skilled in the art and are intended to be included with in the scope of the present invention in any way.

Example-1

Preparation of Candesartan Cilexetil (with Isolation of Cilexetil Trityl Candesartan)

Step-I: Preparation of Trityl Candesartan

To solution of Candesartan (100 g in 350 ml MDC) and triethyl amine (34.3 g) Trityl chloride (76.8 g in 150 ml MDC) is added slowly at temperature of 25-30° C. Temperature of the reaction mass is raised and maintained at reflux temperature for 2 hrs. Reaction mass is cooled to temperature of 30-35° C., water (100 ml) is added, stirred for about 15 min, allowed to settle and separated the layers. Aqueous layer is extracted with MDC (2×100 ml), combined organic layer is washed with water and MDC is removed below 50° C. from organic layer. Ethyl acetate (600 ml) is added, raised and maintained the temperature of the reaction mass at reflux temperature for 2 hrs. The temperature of the mass is cooled, maintained for 1 hr at 25-30° C. and isolated the product by filtration. Wet cake is washed with ethyl acetate (100 ml) and dried at temperature of 45-50° C. to constant weight.

The weight of trityl candesartan is 130 g (Yield 83.8%)

Step-2: Preparation of Trityl Candesartan Cilexetil

Carbohexyl 1-chloroethyl carbonate (36 g) is added to a suspension of trityl candesartan (100 g), potassium carbonate (24 g) and potassium iodide (12 g) in DMSO (500 ml) at temperature of 60-65° C. over 30 min. Reaction mass is maintained at 60-65° C. for 2 hrs, added toluene (300 ml) and water (300 ml). Reaction mass is mixed for 15 min., allowed to settle, the layers are separated at 60-65° C. and aqueous layer is extracted with toluene (200 ml). Water (200 ml) washings are given to the combined organic layer and toluene extractions twice at temperature of 60-65° C. Toluene is distilled off from water washed organic layer at temperature below 60° C. under vacuum, ethanol (100 ml) is added, mixed for about 30 min and distilled off solvents under vacuum at temperature below 60° C. under vacuum. Residue is cooled to 30-35° C., ethanol (300 ml) is added, mixed for 2 hrs at 25-30° C. and filtered the product. Wet cake is washed with ethanol (100 ml) and suck dried. Wet weight of Cilexetil trityl candesartan is 180 g Step-3: Preparation of Cilexetil Candesartan Boric acid (9.0 g) is added to a suspension of Cilexetil trityl candesartan (wet wt, 180 g) in ethanol (1000 ml) at temperature of 25-30° C., temperature of reaction mass is raised and maintained at reflux temperature for 8 hrs. Reaction mass is concentrated to one third of its original volume by distillation of solvent and cooled the solution to 25-30° C. n-Hexane (500 ml) is added to the reaction mass, stirred for 8 hrs at 25-30° C. and filtered the product. Wet cake is washed with n-hexane (100 ml) and dried the material at a temperature of 45-50° C. till constant weight.

Dry weight of Cilexetil candesartan is 70 g (Yield: 78.0%)

Example 2

Preparation of Candesartan Cilexetil (without Isolation of Cilexetil Trityl Candesartan)

Carbohexyl 1-chloroethyl carbonate (36 g) is added to a suspension of trityl candesartan (100 g), potassium carbonate (24 g) and potassium iodide (12 g) in DMSO (500 ml) at temperature of 60-65° C. over 30 min. Reaction mass is maintained at 60-65° C. for 2 hrs, added toluene (300 ml) and water (300 ml). Reaction mass is mixed for 15 min., allowed to settle, the layers are separated at 60-65° C. and aqueous layer is extracted with toluene (200 ml). Water (200 ml) washings are given to the combined organic layer and toluene extractions twice at temperature of 60-65° C. Toluene is distilled off from water washed organic layer at temperature below 60° C. under vacuum, ethanol (100 ml) is added, mixed for about 30 min and distilled off solvents under vacuum at temperature below 60° C. under vacuum. Residue is cooled to 30-35° C., ethanol (1000 ml) and boric acid (9.0 g) is added at temperature of 25-30° C., temperature of reaction mass is raised and maintained at reflux temperature for 8 hrs. Reaction mass is concentrated to one third of its original volume by distillation of solvent and cooled the solution to 25-30° C.

n-Hexane (500 ml) is added to the reaction mass, mixed for 8 hrs at 25-30° C. and filtered the product. Wet cake is washed with n-hexane (100 ml) and dried the material at temperature of 45-50° C. till becomes constant weight.

Dry weight of Cilexetil candesartan is 65 g (Yield: 72.5%)

Example 3

Preparation of Crystalline Type-C Cilexetil Candesartan

Cilexetil candesartan (100 g) is suspended in acetone (600 ml), temperature is raised and maintained at reflux temperature for 30 min. Cooled the reaction mass to 40-45° C. and filtered the mass to remove insolubles. Water (120 ml) is added slowly over 30 min at 40-45° C., gradually cooled the mass to 25-30° C. and water (120 ml) is added slowly over 30 min at 25-30° C. Reaction mass is maintained at temperature of 25-30° C. for 4 hrs, filtered the product, washed the wet cake with a mixture of acetone:water (100:40) and dried the wet cake at temperature of 45-50° C. under vacuum till becomes constant weight.

Dry weight of Crystalline Type-C Cilexetil candesartan is 90 g (Yield: 90%)

The crystallinity is identified by its XRD pattern.

We claim:

1. An improved process for the preparation of candesartan cilexetil comprising the steps of:
   a. treating candesartan with trityl chloride to get trityl candesartan
   b. reacting, the trityl candesartan with cilexetil chloride in dimethyl sulfoxide (DMSO) in the presence of a base to afford trityl candesartan cilexetil; and
   c. deprotecting the trityl candesartan cilexetil in the presence of an inorganic acid selected from phosphoric acid and boric acid in a solvent medium at a temperature of 45° C. to reflux temperature to get candesartan cilexetil.

2. The process as claimed in claim 1, wherein the trityl candesartan is prepared in methylene chloride (MDC) in the presence of triethyl amine.

3. The process as claimed in claim 1, wherein the base utilized in step b) is an inorganic base selected from potassium carbonate and sodium carbonate.

4. The process as claimed in claim 1, wherein in step b) the trityl candesartan cilexetil is isolated from ethanol.

5. The process as claimed in claim 1, wherein the deprotection of trityl candesartan cilexetil is carried out by;
   a. suspending the trityl candesartan cilexetil in ethanol;
   b. adding at least one inorganic acid selected from phosphoric acid and boric acid;
   c. maintaining the reaction mass at a temperature of 45° C. to reflux temperature;
   d. concentrating the reaction mass to about ½ to ¼ of its original volume;
   e. adding an antisolvent selected from the group of C5-C7 hydrocarbons; and
   f. maintaining the mass at about 10° C. to 55° C. to get candesartan cilexitil.

6. The process as claimed in claim 1, wherein the obtained candesartan cilexetil is further purified by dissolving in acetone and precipitation by an addition of water.

7. The process as claimed in claim 6, wherein the obtained candesartan cilexetil is in the form of Type-C crystals.

8. The process of claim 5 wherein the antisolvent is selected from hexane and heptane.

9. The process of claim 5 wherein in step f) the mass is maintained at a temperature of about 15° C. to 30° C.

* * * * *